(12) United States Patent
Peterson

(10) Patent No.: US 9,868,107 B1
(45) Date of Patent: Jan. 16, 2018

(54) REMOVAL OF NITROGEN DIOXIDE FROM GAS ENVIRONMENTS USING METAL-ORGANIC FRAMEWORKS

(71) Applicant: U.S. Army Edgewood Chemical Biological Center, APG, MD (US)

(72) Inventor: Gregory W Peterson, Belcamp, MD (US)

(73) Assignee: The United States of America as Represented by the Secretary of the Army, Washington, DC (US)

(*) Notice: Subject to any disclaimer, the term of this patent is extended or adjusted under 35 U.S.C. 154(b) by 0 days.

(21) Appl. No.: 15/430,740

(22) Filed: Feb. 13, 2017

Related U.S. Application Data

(60) Provisional application No. 62/306,229, filed on Mar. 10, 2016.

(51) Int. Cl.

| | |
|---|---|
| *B01D 53/56* | (2006.01) |
| *B01D 46/00* | (2006.01) |
| *B01D 39/00* | (2006.01) |
| *B01J 20/22* | (2006.01) |
| *B01J 8/02* | (2006.01) |
| *C01C 1/12* | (2006.01) |
| *C07F 15/02* | (2006.01) |
| *C07F 11/00* | (2006.01) |
| *C07F 7/28* | (2006.01) |
| *C07F 5/06* | (2006.01) |
| *C07F 3/04* | (2006.01) |
| *C07F 3/02* | (2006.01) |

(52) U.S. Cl.
CPC .............. *B01J 20/226* (2013.01); *B01J 8/02* (2013.01); *C01C 1/12* (2013.01); *C07F 3/02* (2013.01); *C07F 3/04* (2013.01); *C07F 5/06* (2013.01); *C07F 7/28* (2013.01); *C07F 11/00* (2013.01); *C07F 15/02* (2013.01)

(58) Field of Classification Search
CPC .. B01D 53/56; B01D 53/565; B01D 2239/02; B01D 2253/204; B01D 2255/705; B01D 2257/404; B01D 2258/0283; B01D 2258/06; B01D 46/00; B01D 39/16; B01D 39/00
See application file for complete search history.

(56) References Cited

U.S. PATENT DOCUMENTS

| | | | |
|---|---|---|---|
| 8,633,331 B2* | 1/2014 | Bandosz | B01D 53/40 252/184 |
| 2012/0129684 A1* | 5/2012 | Vimont | B01D 53/8628 502/170 |
| 2012/0204719 A1* | 8/2012 | Dubois-Brugger | B01D 53/02 95/129 |
| 2017/0087531 A1* | 3/2017 | Long | B01J 20/226 |

\* cited by examiner

*Primary Examiner* — Timothy C Vanoy
(74) *Attorney, Agent, or Firm* — Ulysses John Biffoni

(57) ABSTRACT

Provided are materials and processes for removing nitrogen dioxide gas from a sample by contacting the sample with a filtration media that includes a MOF, optionally an amine containing MOF. The resulting filtration media has the ability to sequester nitrogen dioxide with little conversion to nitric oxide, is stable, and highly functional so as to be useful in protective equipment or other filtration systems.

24 Claims, 10 Drawing Sheets

REMOVAL OF NITROGEN DIOXIDE FROM GAS ENVIRONMENTS USING METAL-ORGANIC FRAMEWORKS

REFERENCE TO RELATED APPLICATIONS

This application claims the benefit of and priority from U.S. Provisional Application Ser. No. 62/306,229 filed on Mar. 10, 2016.

U.S. GOVERNMENT INTEREST

The invention described herein may be manufactured, used and licensed by or for the U.S. Government.

FIELD

This invention relates generally to air filtration and filtration media.

BACKGROUND

Various vehicles and industries, including those involving coal-fired electrical power generation, wood processing, and oil and gas production, produce nitrogen oxide gases (e.g., NO, $N_2O$, $NO_2$, and $N_2O_4$). Nitrogen oxides (collectively referred to as $NO_x$), and particularly, nitrogen dioxide, are primary air pollutants and among the most common toxic pollutants generated on earth. The continual generation of such materials provokes considerable interest in the development of efficient, cost effective technologies to remediate $NO_x$-containing emissions such as in flue gas scrubbing operations, in protection based operations such as those required by workers, or for sensitive equipment.

Emergency workers such as first responders and clean-up workers require protection against nitrogen oxide gases due to its common production from combustion/fires. The common respirators available to these individuals, which typically rely on activated carbon as a filtration media, provide relatively poor protection and removal capabilities for these gasses. Some improvement has been observed by the use of zeolites and titania. These materials, however, suffer from several drawbacks.

As such, there is a need for improved materials capable of removing or sequestering nitrogen dioxide. The inclusion of such materials in filtration apparatuses or safety systems such as breathing apparatuses is greatly desired.

SUMMARY

The following summary of the invention is provided to facilitate an understanding of some of the innovative features unique to the present invention and is not intended to be a full description. A full appreciation of the various aspects of the invention can be gained by taking the entire specification, claims, drawings, and abstract as a whole.

Provided are devices and methods for the filtration or other removal of nitrogen dioxide from a gaseous area or sample. A process in some aspects includes contacting or moving a gaseous sample comprising a nitrogen dioxide to or through a filter, surface, building material, or device comprising a filtration media, said filtration media comprising a metal organic framework (MOF), said filtration media suitable to react with the nitrogen dioxide, optionally to reduce the concentration of nitrogen dioxide in the gaseous sample thereby decreasing the amount of nitrogen dioxide in the sample. A MOF in some aspects includes a functional group capable of reacting with nitrogen dioxide, optionally an amine functional group. In some aspects the MOF includes or is UiO-66-$NH_2$, optionally to the exclusion of other MOFs, or other filtration media, optionally with the proviso that the MOF is the only filtration media or combined with a carbon material, optionally activated carbon. A sample is optionally air or combustion exhaust. Illustrative MOFs optionally include a metal. A metal is optionally selected from the group of: Al, Cr, Fe, Hf, Mn, Ti, V, Zr, Ca, and Mg. Optionally, a metal is Zr alone, Ti alone, or combinations thereof with no other metal in the MOF. In some aspects, a MOF has an average pore volume of 0.1 $cm^3/g$ or greater. Optionally, the MOF has a surface area in excess of 600 $m^2/g$ as measured by a Brunauer Emmett Teller (BET) technique. Optionally, the MOF has a capacity for absorbing nitrogen dioxide of 9 moles $NO_2$ per kilogram MOF or greater. A process is optionally performed at a temperature of 20° C. to 30° C., but optionally may be performed at elevated temperatures, optionally up to 400° C. In some aspects, an MOF is combined with a second MOF, a second other filter material, or both. A filter material optionally includes carbon, optionally an activated carbon. In some aspects, a filter is a building material.

Also provided are devices for reducing the level of a contaminant in a gas. In some aspects a device is a filter capable of reducing nitrogen dioxide in sample, an environmental area, or a flow of gas, optionally at a temperature of 10 degrees Celsius to 50 degrees Celsius. A device optionally includes an amine modified porous metal organic framework (MOF), the MOF comprising a metal selected from the group consisting of Zr and Ti, and a carbon filtration media. The MOF optionally has an average pore volume of 0.1 $cm^3/g$ or greater. The MOF optionally has a surface area in excess of 600 square meters per gram as measured by a Brunauer Emmett Teller (BET) technique. In some aspects, the MOF used in the filter has a capacity for absorbing nitrogen dioxide of 9 moles per kilogram or greater. The MOF is optionally located within the filter adjacent to the carbon filtration media, optionally directly adjacent to the carbon filtration media, optionally intermixed with the carbon filtration media. In some aspects, the MOF is directly on the carbon filtration media proximal to a nitrogen dioxide source.

DETAILED DESCRIPTION

Figure 1A:
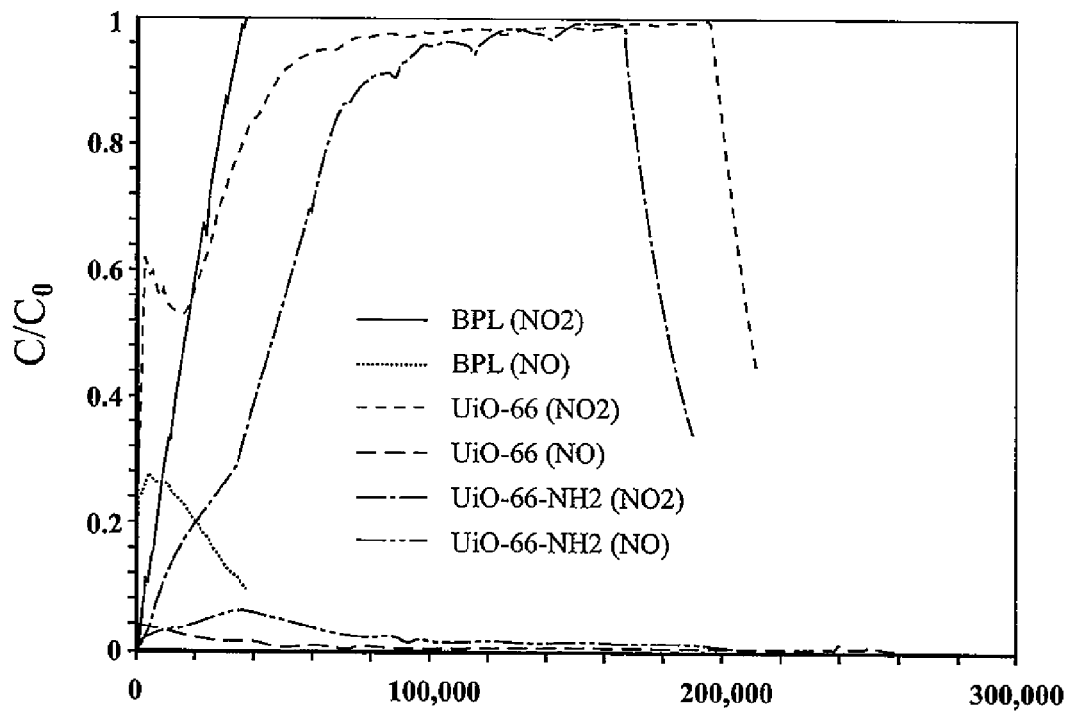
FIG. 1A illustrates microbreakthrough curves of nitrogen dioxide through BPL activated carbon, UiO-66, and UiO-66-$NH_2$ under low relative humidity conditions.

The following description of particular aspect(s) is merely exemplary in nature and is in no way intended to limit the scope of the invention, its application, or uses, which may, of course, vary. The invention is described with relation to the non-limiting definitions and terminology included herein. These definitions and terminology are not designed to function as a limitation on the scope or practice of the invention but are presented for illustrative and descriptive purposes only. While the processes or compositions are described as an order of individual steps or using specific materials, it is appreciated that steps or materials may be interchangeable such that the description of the invention may include multiple parts or steps arranged in many ways as is readily appreciated by one of skill in the art.

It will be understood that, although the terms "first," "second," "third" etc. may be used herein to describe various elements, components, regions, layers, and/or sections, these elements, components, regions, layers, and/or sections should not be limited by these terms. These terms are only used to distinguish one element, component, region, layer, or section from another element, component, region, layer, or section. Thus, "a first element," "component," "region," "layer," or "section" discussed below could be termed a second (or other) element, component, region, layer, or section without departing from the teachings herein.

The terminology used herein is for the purpose of describing particular embodiments only and is not intended to be limiting. As used herein, the singular forms "a," "an," and "the" are intended to include the plural forms, including "at least one," unless the content clearly indicates otherwise. "Or" means "and/or." As used herein, the term "and/or" includes any and all combinations of one or more of the associated listed items. It will be further understood that the terms "comprises" and/or "comprising," or "includes" and/or "including" when used in this specification, specify the presence of stated features, regions, integers, steps, operations, elements, and/or components, but do not preclude the presence or addition of one or more other features, regions, integers, steps, operations, elements, components, and/or groups thereof. The term "or a combination thereof" means a combination including at least one of the foregoing elements.

Unless otherwise defined, all terms (including technical and scientific terms) used herein have the same meaning as commonly understood by one of ordinary skill in the art to which this disclosure belongs. It will be further understood that terms such as those defined in commonly used dictionaries, should be interpreted as having a meaning that is consistent with their meaning in the context of the relevant art and the present disclosure, and will not be interpreted in an idealized or overly formal sense unless expressly so defined herein.

The novel processes described herein involve contacting gaseous sample, optionally in the form of contaminated air, where the sample includes nitrogen dioxide ($NO_2$), with a filtration material capable of reacting with and removing the nitrogen oxide, with a relatively low conversion rate to nitric oxide, which is a problem with prior methods of $NO_2$ scrubbing. Illustrative examples of nitrogen oxides are in gaseous form. Optionally, a nitrogen oxide includes but are not limited to NO, $N_2O$, $NO_2$, and $N_2O_4$, and the like. While much of this disclosure is directed to filtration media for the purpose of removing $NO_2$ from a gas such as air, it is equally appreciated that a filtration media as provided herein may be used for other filtration purposes such as in catalytic converters, or directly added to a material such as building material to reduce nitrogen dioxide emissions from that building material.

The nitrogen dioxide is removed from a gas by contact with a filtration media. A filtration media as provided herein includes one or more metal organic framework(s) (MOF) either within the filtration media or as a component thereof. MOFs are comprised of secondary building units (SBU), typically made from metal oxide clusters connected by organic linkers. The resulting structure is an extended, 3-dimensional framework that is often highly porous. Due to the ability to change/tune both the SBU (e.g., changing metal type) and organic linker (e.g. putting functional groups on the linker, using larger/bulkier/longer linkers), the formation of several type of MOF structures is possible. The preferred MOFs used as in a filtration media include amine-containing MOFs.

There are multiple sub-groups of MOFs, such as isoreticular MOFs (IRMOFs), materials from institute Lavoisier (MIL) MOFs, zeolitic imidazolate frameworks (ZIFs), and others. Typically these groups are based on similarities of the structures. For example, most of the IRMOFs contain zinc acetate SBUs, and changing the linker results in a wide range of porous structures. IRMOFs in particular are not stable to water, however.

UiO-66-type MOFs which may be used herein are structures originally synthesized at the University of Oslo. UiO-66-type MOFs include zirconium-based SBUs, and this series of MOFs is particularly stable to water as well as acidic conditions. UiO-66 utilizes a terephthalic acid (a.k.a. benzene dicarboxylate) linker that can be functionalized with a variety of groups, such as an amine group (herein known as UiO-66-$NH_2$). MIL MOFs, although typically utilizing different metals such as iron, chromium, and aluminum, can also be functionalized with amine groups. As such, a MOF as used in a filtration media herein is optionally an amine containing MOF whereby the amine is present in the MOF as a functional group capable of reacting with nitrogen dioxide.

In some examples, a MOF is a UiO-66 analog such as UiO-66-$NH_2$. UiO-66 MOFs are formed of $Zr_6O_4(OH)_4$ octahedra that are 12-fold connected to adjacent octahedra through a 1,4-benzene-dicarboxylate (BDC) linker, resulting in a highly packed face centered cubic (fcc) structure. Methods of forming such MOFs including amine-containing MOFs are illustratively presented in *J. Am. Chem. Soc.*, 130, 13850 (2008), *Chem. Commun.*, 46, 7700 (2010), and U.S. Pat. No. 9,175,025 B2. In some aspects, a MOF is a Zn (DABCO) MOF or PCN-250. These and other operable MOFs as well as illustrative methods of synthesis of such MOFs may be found in Stock and Biswas, *Chem. Rev.*, 2012; 112 (2):933-969 and Feng, D. et al., *Nat. Commun.* 5:5723 dol: 10.1038/ncomms6723 (2014).

A MOF includes a metal. A metal is optionally. Al, Cr, Fe, Hf, Mn, Ti, V, Zr, Ca and Mg, or other metal. In some aspects, a metal is Zr or Ti. Optionally, a metal is Zr.

A MOF has a porous structure. Pore volume (optionally average pore volume) of an MOF is optionally at or greater than 0.1 cubic centimeters per gram ($cm^3/g$), optionally at or greater than 0.3 $cm^3/g$. In some aspects, pore volume is 0.1 $cm^3/g$ to 1.2 $cm^3/g$, or any value or range therebetween, optionally 0.3 $cm^3/g$ to 1.2 $cm^3/g$, optionally 0.1 $cm^3/g$ to 0.9 $cm^3/g$, optionally 0.3 $cm^3/g$ to 0.9 $cm^3/g$.

A MOF has a surface area. Increased surface area correlates with improved separation capability and reactability of the MOF used in a filtration media. Surface areas of exemplary MOFs as measured using the Brunauer Emmett Teller (BET) technique are optionally in excess of 600 square meters per gram ($m^2/g$). In some aspects, a surface area is at or in excess of 700 $m^2/g$, optionally 800 $m^2/g$, optionally 900 $m^2/g$, optionally 1000 $m^2/g$, optionally 1100 $m^2/g$, optionally 1200 $m^2/g$, optionally 1300 $m^2/g$, optionally 1400 $m^2/g$, optionally 1500 $m^2/g$, optionally 2000 $m^2/g$, optionally 3000 $m^2/g$, optionally 4000 $m^2/g$, optionally 5000 $m^2/g$. In some aspects, the BET surface area of a MOF is between 800 $m^2/g$ and 1100 $m^2/g$.

A MOF as used for filtration of nitrogen dioxide optionally has a capacity for absorbing or adsorbing the nitrogen dioxide suitable for acting in a filtration system. In some aspects the nitrogen dioxide capacity is at or in excess of 8.8 moles $NO_2$ per kilogram MOF (mol/kg) when the material is dry. Optionally, the nitrogen dioxide capacity is in excess of 9 mol/kg, optionally 10 mol/kg, optionally 11 mol/kg, optionally 12 mol/kg, optionally 13 mol/kg, optionally 14 mol/kg, optionally 15 mol/kg, optionally 16 mol/kg, optionally 17 mol/kg, optionally 18 mol/kg, optionally 19 mol/kg, optionally 20 mol/kg, optionally 21 mol/kg, optionally 22 mol/kg, optionally 23 mol/kg, optionally 24 mol/kg, optionally 25 mol/kg.

An additional advantage of using a MOF as a filtration media is the ability of the MOF to reduce nitrogen dioxide at an ambient temperature, optionally from 10 degrees Celsius to 37 degrees Celsius (° C.). In some aspects, however, the MOF may be used to reduce nitrogen dioxide at temperatures higher than ambient temperature, optionally to temperatures up to 300° C. As such, a MOF is optionally contacted to a nitrogen dioxide source at a reaction temperature. A reaction temperature is optionally from 0° C., to 400° C. or greater. A reaction temperature is optionally from 0° C. to 300° C., optionally 0° C. to 200° C., optionally 0° C. to 100° C., optionally 10° C. to 50° C., optionally 20° C. to 40° C., optionally 20° C. to 38° C., optionally 20° C. to 30° C., optionally room temperature defined as 25° C. or within 5° C. thereof.

A MOF as provided herein is used alone as a filtration media, or as a component of a filtration media that includes one or more additional materials capable of filtering, separating, absorbing or otherwise dealing with unwanted molecular materials. Filtration media may be in many forms, such as for example beads, extrudates, granules, etc. Filtration media may be housed in respirator bodies such as, for example, when being used in individual protection filters in respirators and gas masks. Alternatively, the filtration media may be housed in a larger bed such as for example when employed in collective protection applications such as shelters, and still larger bodies, such as for example when employed in treating industrial waste streams. The design of the bed can be of many forms and configurations such that contact between the nitrogen dioxide containing gas or fluid and the media is brought about.

When a MOF is used as a filtration media in a filter apparatus, it is present at a bed depth where bed depth is directionally oriented along (e.g. substantially parallel with) the flow path of a gas source. A bed depth is optionally 0.5 mm to 1 cm or any value or range therebetween. Optionally, a bed depth is greater than 1 cm. A bed depth is optionally in excess of 2 mm, optionally from 2 to 6 mm, optionally from 4 to 6 mm. Optionally, a bed depth does not exceed 6 mm.

The flow of the nitrogen dioxide containing gas or fluid through the bed of media should be sufficient to allow for the desired amount of nitrogen dioxide to be removed prior to breakthrough being achieved. Breakthrough, a term well known to one skilled in the art, refers to the point in the process when the concentration of the toxic chemical in the filter effluent stream exceeds a threshold value. Breakthrough time, another term well known to one skilled in the art, refers to the time from the start of the chemical challenge to the point in time where the effluent concentration of toxic chemical exceeds the threshold value, often referred to as the breakthrough concentration. The residence time of the process stream within the filter bed can vary greatly depending on the application. The residence time can range from less than 0.1 seconds to greater than 10 seconds; however, for respirator applications, the preferred residence time is on the order of 0.1 seconds to 0.35 seconds and more preferably on the order of 0.1 seconds to 0.2 seconds. For collective protection applications, the residence time is consistent, although slightly greater than residence times employed in respirator applications. For industrial applications, such as for example those involving the filtration of ammonia and/or sulfur dioxide from waste streams, the residence time may be quite large, depending on the concentration of contaminant in the waste stream and the desired period between filter change-out.

For many applications, such as chemical filtration, it is desired that the MOF be in an engineered form, such as for example beads, granules, cylinders, etc. Forming the MOF powder into an engineered form can be accomplished using techniques known to one skilled in the art. One technique involves briquetting or tableting the MOF powder using an appropriate device, such as for example a roll compactor or a tableting machine. The resulting briquettes or tablets are then ground using such as for example a hammer mill or jaw crusher to reduce the briquettes or tablets into granules. Product granules are then sieved to the appropriate mesh, size, such as for example 6×12 mesh, 12×30 mesh, 20×40 mesh, 40×140 mesh, etc.

In some aspects, a MOF is combined with an additional filtration media. An additional filtration media optionally includes an additional filter material. In some aspects, a MOF may be layered with or within, separate from, or intermixed with a filter material. In some aspects, a MOF is placed in close proximity to a filter material, optionally on a filter material, optionally directly on a filter material and thereby contacting the filter material. Illustrative examples of a filter material include carbon such as activated impregnated carbon, among others. A MOF may be placed at multiple locations within a bed of filter material such that as a nitrogen dioxide gas penetrates the filter material, it also comes into contact with the MOF. A MOF is optionally layered on or directly on a filter material. In some aspects, a MOF is layered on or directly on a filter material positioned on a surface expected to contact nitrogen dioxide prior to the filter material. In some aspects, a MOF is layered on or directly on a filter material positioned on a surface expected to contact nitrogen dioxide following contact with the filter material.

The resulting MOF is thereby capable of binding to and optionally reacting with nitrogen dioxide while producing relatively small amounts of nitric oxide. The combination with a filter material allows sequestering and removal of the small amounts of nitric oxide thereby improving the effectiveness of the overall filter material. Optionally, a filter incorporating a MOF is a monolithic filter meaning that the filter includes a single filtration media, in this case the MOF. Optionally, the MOF is used as a layer within or upon the filtration media such that it is used as either a primary reactant layer or a polishing layer depending on whether the MOF is located on a stream front face or a stream rear face of the filter, or otherwise within the other filtration media.

In some aspect, a MOF is used as a component of a building material. A building material is any known material such as a natural or synthetic material. Optionally, a building material is a concrete material, polymeric material, wood material, coating such as a paint, varnish, or other coating. The MOF is optionally located on a surface of a building material so as to be capable of reacting with nitrogen dioxide produced or otherwise within an atmosphere the building material is in contact with.

In other aspects, a MOF is located in proximity to a combustion source, optionally an engine or manufacturing facility. A MOF is optionally located in or in proximity to a catalytic converter for filtering of nitrogen dioxide emitted from the source.

EXPERIMENTAL

Synthesis of UiO-66-NH$_2$

UiO-66-NH$_2$ was synthesized by Lawrence Berkeley National Laboratory. A microwave synthesis of the MOF UiO-66-NH$_2$ was prepared using zirconium tetrachloride, 2-aminoterephthalic acid, water and dimethylformamide. The metal salt was purchased from Alfa Aesar. Additional chemicals were purchased from Sigma Aldrich. The molar composition of the reaction is 1 Zr$^{4+}$: 1 2-ATA: 3.17 H$_2$O: 297 DMF.

400 mL of DMF and 2 mL of DI H$_2$O were added slowly to 8.12 g of ZnCl$_4$ in an Erlenmeyer flask (gases are produced upon addition of solvent). In a separate Erlenmeyer flask 400 mL of DMF was added to 6.275 g of 2-aminoterephthalic acid. Both mixtures were stirred until completely dissolved. The solutions were then mixed together and heated by microwave irradiation in sealed vessels at 1500 W for 9 hr at 120° C. The resulting pale yellow powder was filtered and extracted with methanol in a Soxhlet extractor, after which the material was dried in air and then heated in an oven at 65° C. The material was subsequently activated in vacuum at 150° C. for 16 hours.

Microbreakthrough Experiments:

A small breakthrough apparatus was used to evaluate milligram-scale quantities of MOF samples for the adsorption of nitrogen dioxide. Approximately 10-20 mg of material was loaded into a nominal 4 mm i.d. fritted glass tube. The tube was subsequently loaded into a water bath at 20° C. Prior to testing, each MOF was regenerated to remove moisture for one hour at 150° C. under flowing dry air to remove any physisorbed water. A ballast with a predetermined quantity of challenge gas was then mixed with a stream of dry (−40° C. dew point) air at a rate necessary to achieve a challenge concentration of 500-700 ppm. The NO$_2$/air stream was then sent through the fitted glass tube at a flow rate of 20 mL min$^{-1}$, equivalent to a residence time of approximately 0.15 seconds. The effluent stream was sent through a ThermoElectron FTIR. The corresponding breakthrough curve was integrated to determine the loading at saturation.

Figure 1B:
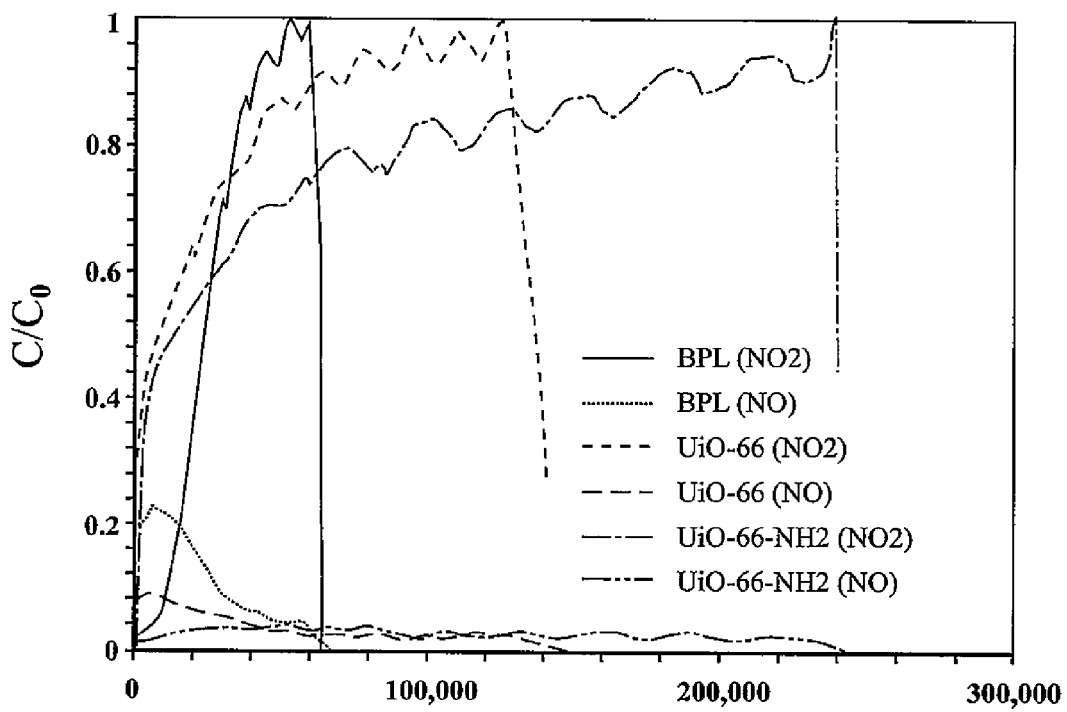
FIG. 1B illustrates microbreakthrough curves of nitrogen dioxide through BPL activated carbon, UiO-66, and UiO-66-$NH_2$ under high relative humidity conditions.

FIG. 1 shows microbreakthrough curves of nitrogen dioxide through BPL activated carbon (Calgon), UiO-66, and UiO-66-NH$_2$ under low (A) and high (B) RH conditions. Table 1 summarizes the breakthrough capacities. Of particular note is that NO$_2$ breaks through BPL faster, and has a lower capacity, as compared to UiO-66-NH$_2$.

TABLE 1

| | | Values | | |
|---|---|---|---|---|
| Condition | Parameter | BPL | UiO-66 | UiO-66-NH$_2$ |
| Dry* | mol/kg | 8.8 | 8.8 | 20.3 |
| | g NO$_2$/g MOF | 0.4 | 0.4 | 0.93 |
| | % NO generated | 25 | 7.5 | 7.6 |
| Humid** | mol/kg | 15.6 | 13.2 | 31.2 |
| | g No$_2$/g MOF | 0.72 | 0.61 | 1.4 |
| | % NO generated | 21 | 19 | 14 |

Figure 2:
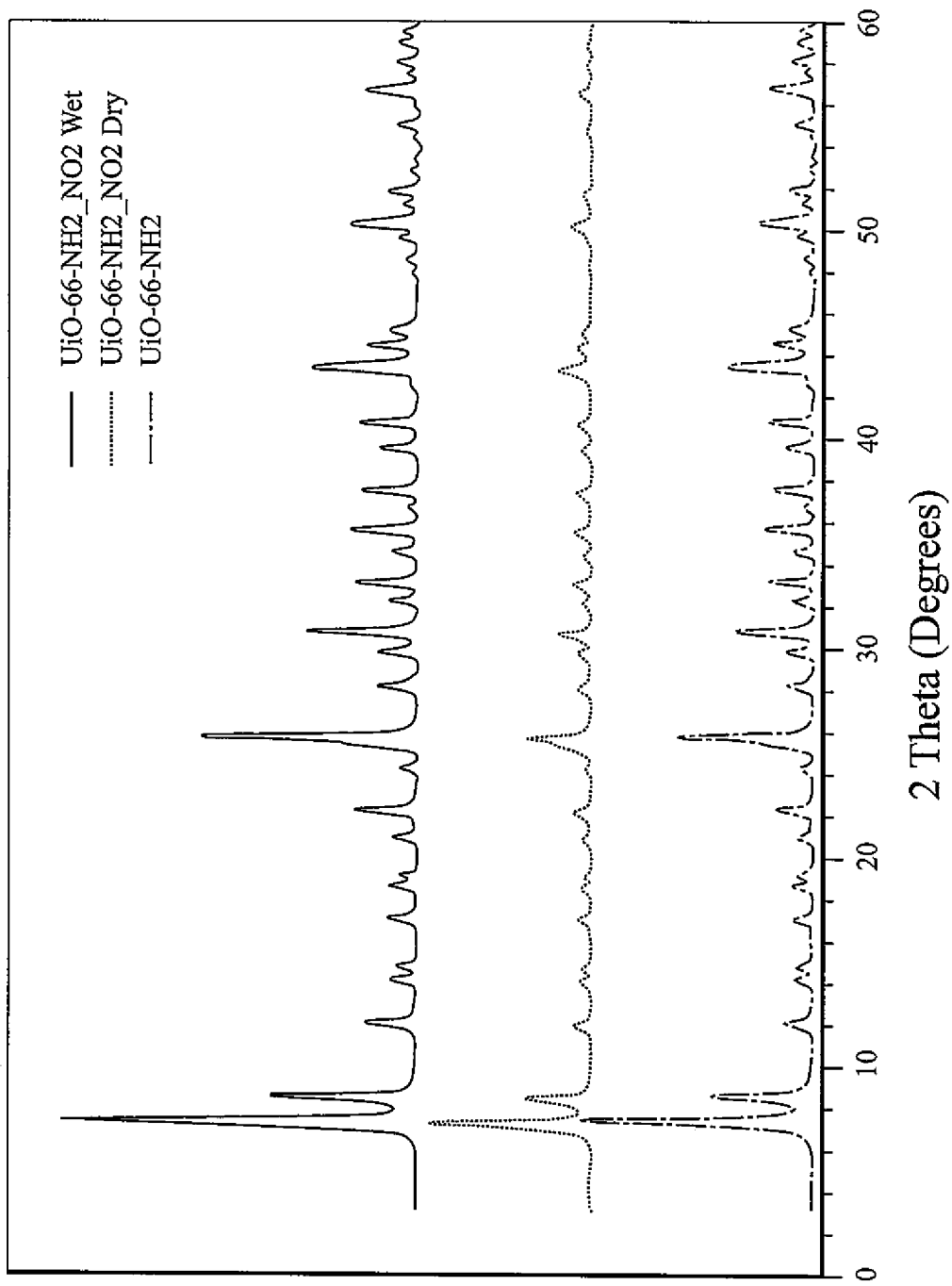
FIG. 2 illustrates PXRD data for UiO-66-$NH_2$ before and after exposure to $NO_2$ demonstrating that the structure remains intact.

*Sample activated at 150° C., tested at 0% RH
**Sample equilibrated at 80% RH, tested at 80% RH Powder X-Ray Diffraction (PXRD):

UiO-66-NH$_2$ prior to and after exposure to NO$_2$ was analyzed using powder X-ray diffraction (PXRD). PXRD measurements were taken using a Rigaku Miniflex 600 X-ray powder diffractometer with a D/Tex detector. Samples were scanned at 40 kV and 15 mA, using Cu Kα radiation ($\lambda$=1.54 Å), and a scan rate of 5° min-1 over a 2θ range of 5 to 50°. PXRD diffraction patterns were processed using the Reflex module in Material Studio 6.1 by Accelrys. Results are illustrated in FIG. 2 demonstrating that the structure of the UiO-66-NH$_2$ remains intact following exposure to nitrogen dioxide allowing for a regenerative filtration system.

N$_2$ Isotherms

Figure 3:
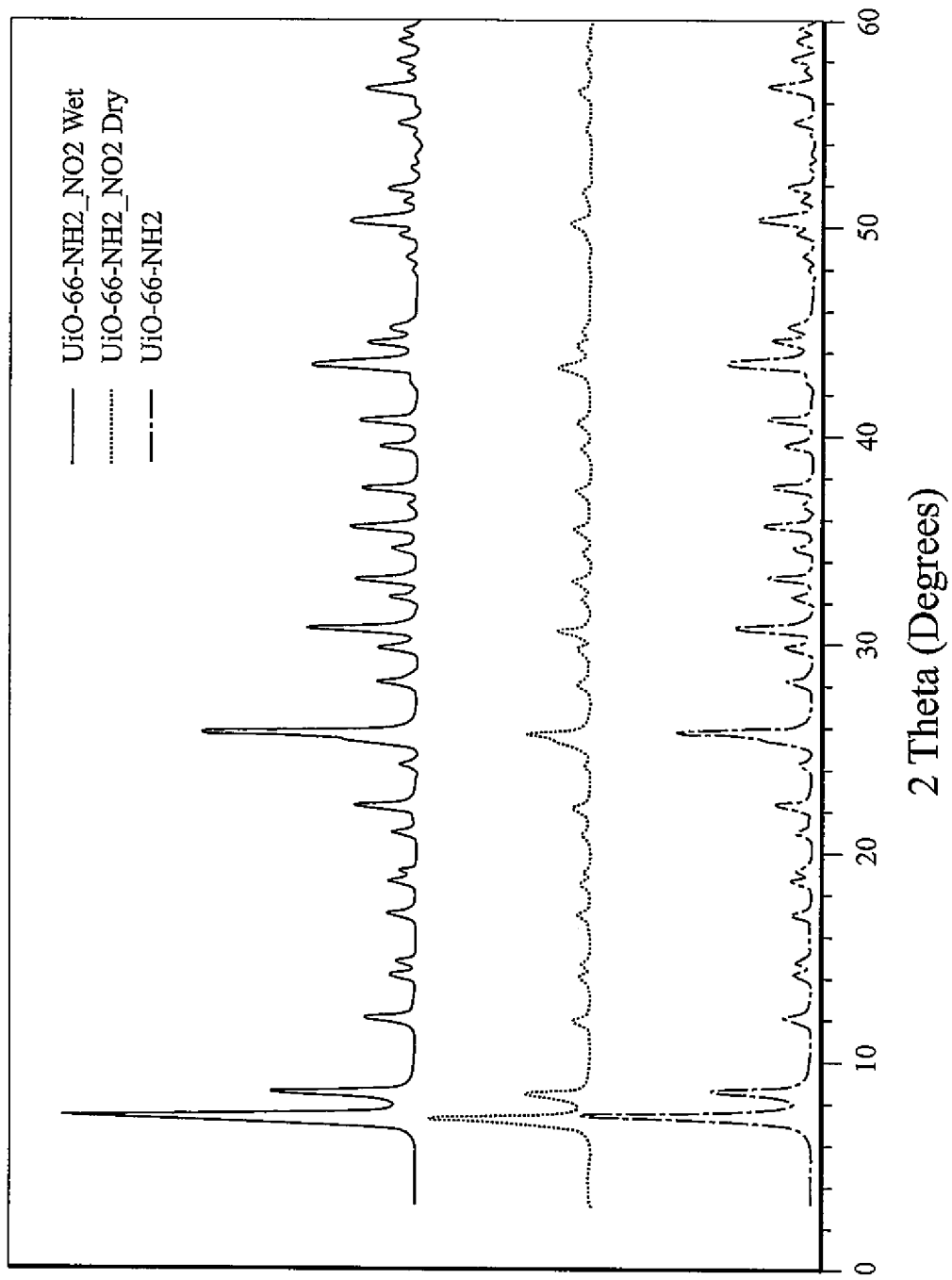
FIG. 3 illustrates Nitrogen isotherm data for UiO-66-$NH_2$ before and after exposure to $NO_2$.

Nitrogen adsorption isotherms were measured for each activated MOF sample using a Micromeritics TriStar 3000 analyzer at 77 K. Prior to analysis, approximately 100 mg of each MOF was activated overnight at 150° C. under a flow of dry nitrogen. The BET method was used to obtain the specific surface area (m$^2$ g$^{-1}$). Results are illustrated in FIG. 3 demonstrating that exposure of UiO-66-NH$_2$ to NO$_2$ results in little observed degradation and excellent nitrogen uptake.

TABLE 2

| Sample | BET Surface Area (m$^2$/g) | Pore Volume (cc/g) |
|---|---|---|
| UiO-66-NH$_2$ | 987 | 0.4 |
| UiO-66-NH$_2$-NO$_2$ exposed, Dry | 832 | 0.33 |
| UiO-66-NH$_2$-NO$_2$ exposed, Dry | 950 | 0.38 |

Figure 4:
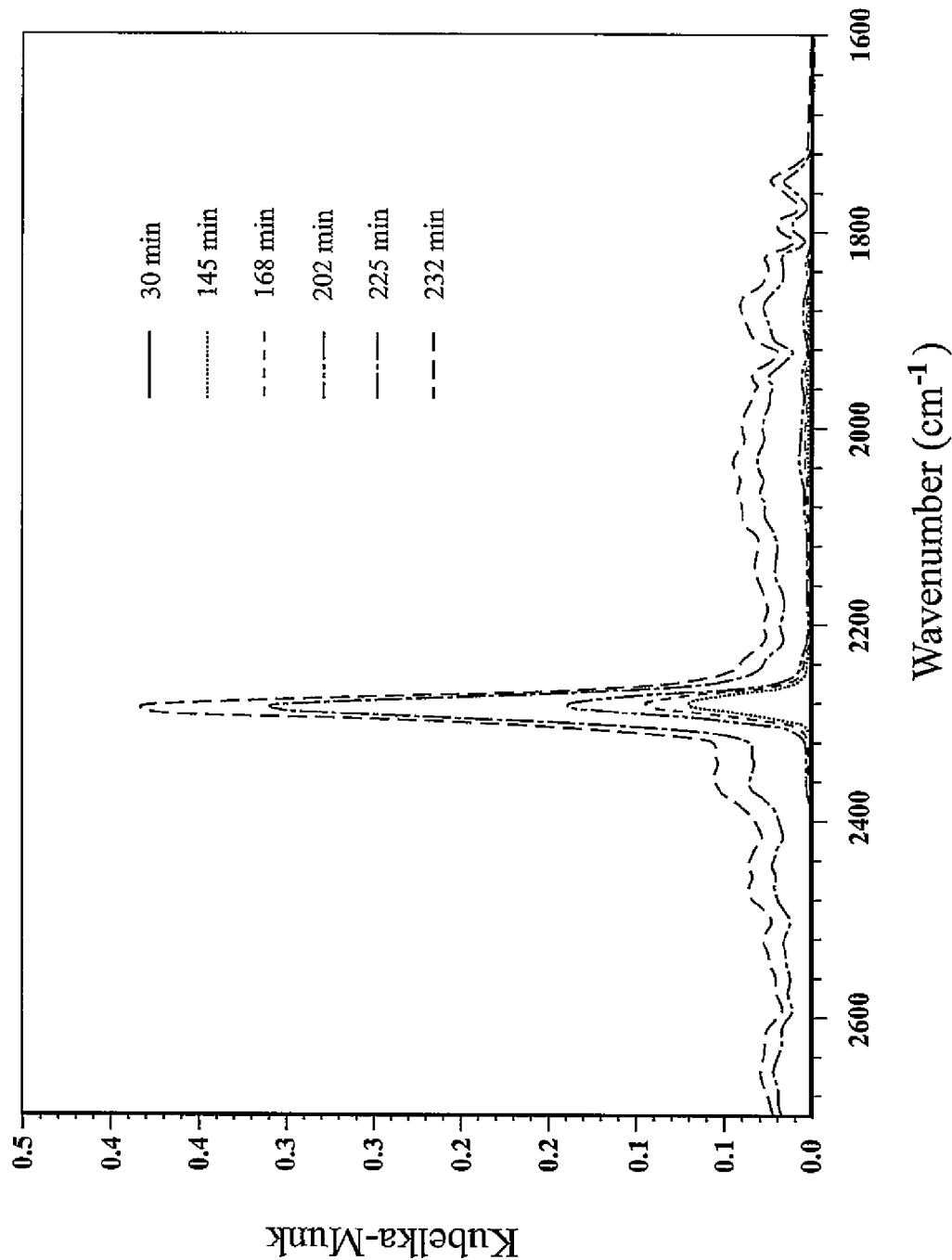
FIG. 4 illustrates diffuse reflectance infrared Fourier transform spectroscopy of UiO-66-$NH_2$ after exposure to $NO_2$.

Diffuse Reflectance Infrared Fourier Transform (DRIFTS) Analyses:

Adsorption of NO$_2$ was analyzed in situ on UiO-66-NH$_2$ with Diffuse Reflectance Infrared Spectroscopy (DRIFTS). 25 mg of UiO-66-NH$_2$ was packed into a 6 mm diameter porous ceramic cup, and the sample was purged in a small stainless steel vessel under dry nitrogen for 24 hours to remove excess water and to provide a stable background for DRIFTS experiments. After the purge, the sample was rapidly transferred to a Pike Technologies DiffuseIR environmental cell with a KBr window, where the sample was maintained at 25° C. under a 10 mL/min ultra-high purity He flow. FTIR spectra were collected using a Thermo Nicolet 6700 spectrometer set with a resolution of 2 cm$^{-1}$ using a liquid nitrogen cooled MCT/A detector. Spectra were collected periodically until it was confirmed that gas phase water and $CO_2$ were no longer present in the cell and that the sample had equilibrated in the He stream (3 hr). After equilibration, a background spectrum (1024 scans) was collected to be used as a reference for the remainder of the experiment. 1,000 ppm $NO_2$ in $N_2$ was introduced to the cell at a flow of 10 mL min$^{-1}$ from a ballast coupled with a flow controller. Spectra were collected in the form of difference spectra, where positive peaks represent newly formed species while negative peaks are indicative of depletion of species near the surface. The results are illustrated in FIG. 4 demonstrating a significant peak indicative of formation of a diazonium ion at the amine group. As a diazonium ion is known to degrade to $N_2$, these results demonstrate the ability to reduce $NO_2$ to $N_2$ at room temperature.

Figure 5:
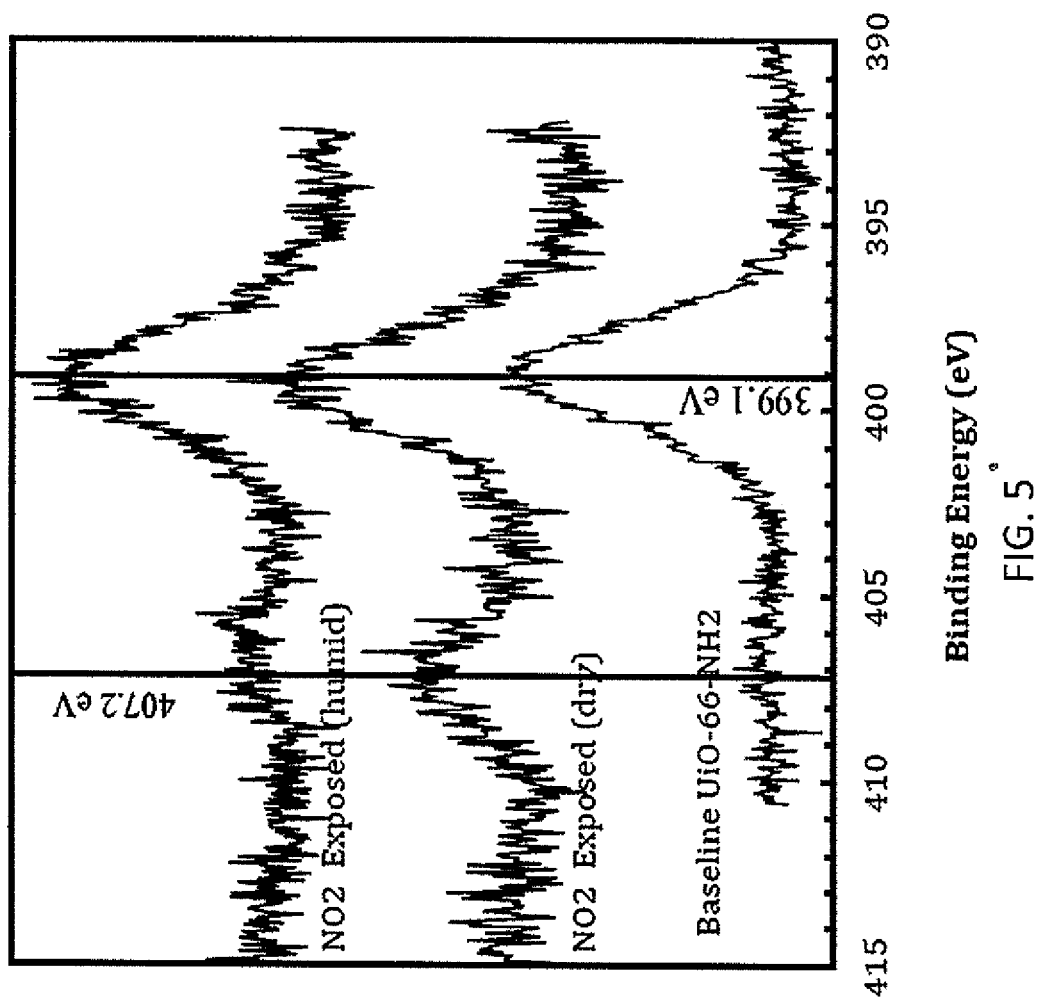
FIG. 5 illustrates the formation of a nitrate on UiO-66-$NH_2$ after exposure to $NO_2$ using XPS.

X-Ray Photoelectron Spectroscopy (XPS):

XPS spectra were recorded using a Perkin Elmer Phi 570 ESCA/SAM system employing MgKα x-rays. All binding energies were referenced to the C1s photoelectron peak at 284.6 eV. Samples of $NO_2$ exposed UiO-66-$NH_2$ were placed on double-stick tape, placed in the chamber, and off-gassed for one hour, and then placed in the chamber for analysis. Results are illustrated in FIG. 5 demonstrating that nitrate is formed on the material. The nitrate can be regenerated/washed off indicating a regenerative system for the scrubbing of environmental $NO_x$.

Figure 6:
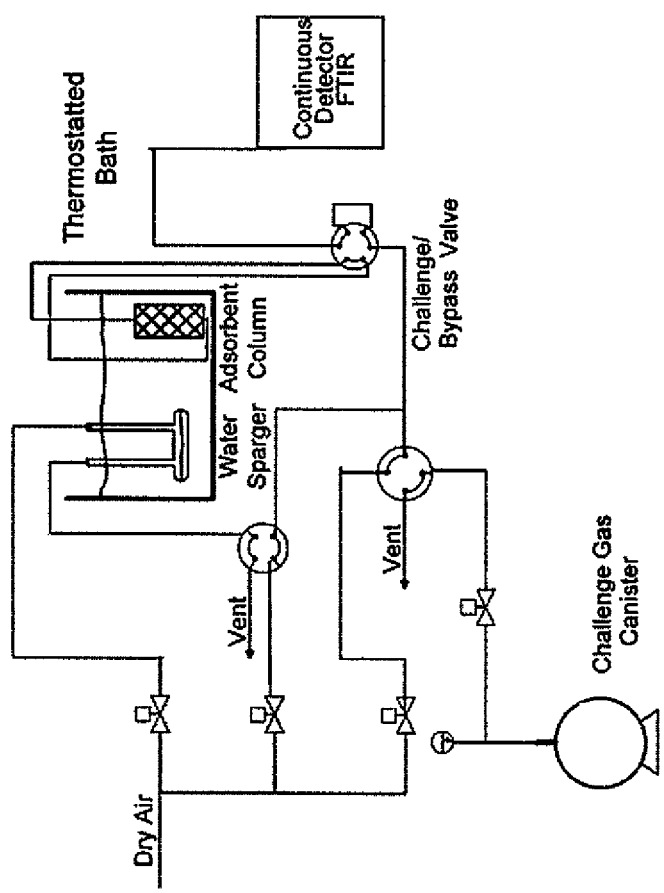
FIG. 6 illustrates an exemplary test apparatus for determining $NO_2$ scrubbing using a filter that incorporates an MOF.
Figure 7:
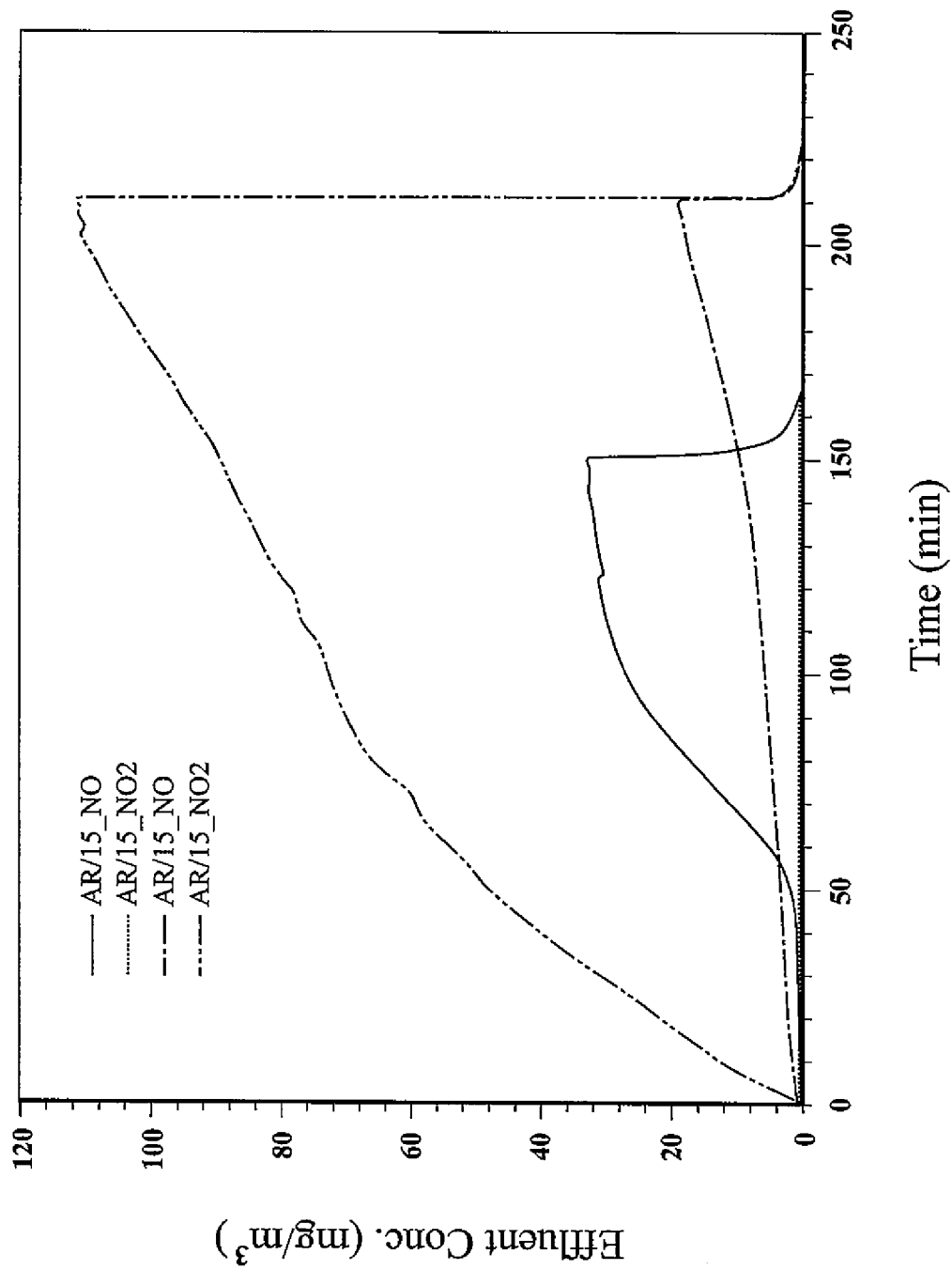
FIG. 7 illustrates $NO_2$ (and NO) breakthrough of granular UiO-66-$NH_2$ in a test apparatus where the material tested was received at either a 15% relative humidity (AR/15) or the material was pre-equilibrated at 80% relative humidity and tested at 80% relative humidity (80/80)

Exposure of Full Filters Containing MOF for Scrubbing $NO_x$:

A test apparatus is created to simulate full scale filters that include a filtration material that includes UiO-66-$NH_2$ placed on top of activated carbon (e.g. proximal to $NO_2$ source) and the filtration of $NO_2$ from a gas stream. A schematic of the test apparatus is illustrated in FIG. 6. The test apparatus is coupled to an FTIR detector for characterization of nitrogen dioxide removal capabilities of a filter. Filters include a 1 cm bed depth of UiO-66-$NH_2$ with a 20×40 mesh material (US standard mesh size). The filter is challenged with $NO_2$ at a concentration of 500 mg/m$^3$ at an airflow velocity of 8.5 cm/s. Results of FTIR analyses using a UiO-66-$NH_2$ only filter material are illustrated in FIG. 7.

Figure 8:
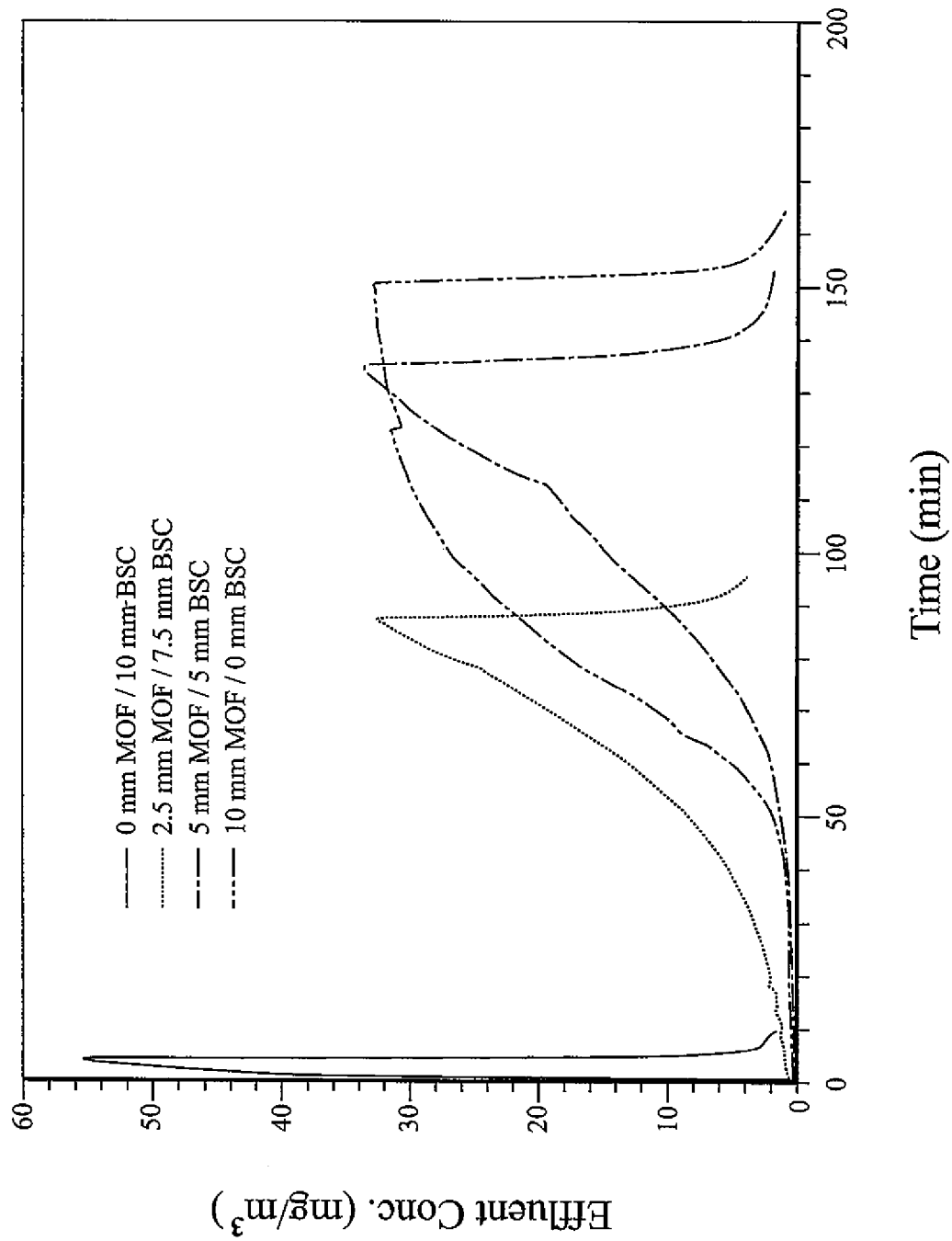
FIG. 8 illustrates $NO_2$ breakthrough of layered bed of UiO-66-$NH_2$ and broad spectrum carbon under 15% RH conditions.

A bed of broad spectrum carbon (BSC, 3M Corporation) is added to the 10 mm test filter at a depth of 0 mm, 2.5 mm, 5 mm, and 10 mm in a position downstream of the UiO-66-$NH_2$. The filters are challenged by $NO_2$ as above under 15% relative humidity. Results are illustrated in FIG. 8. Data show that without any MOF, breakthrough of NO is immediate. Increasing MOF in the bed increases breakthrough time.

Figure 9:
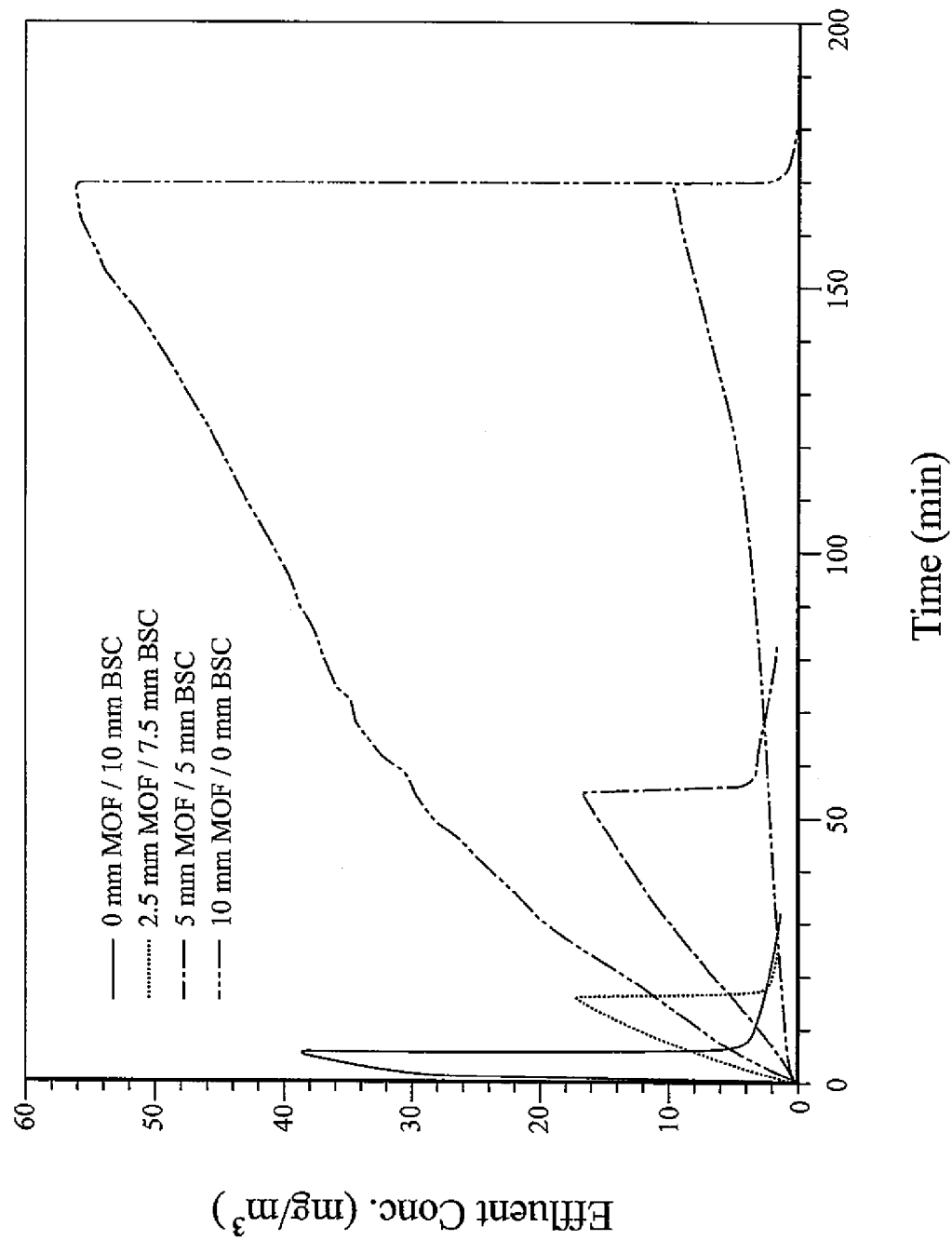
FIG. 9 illustrates $NO_2$ breakthrough of layered bed of UiO-66-$NH_2$ and broad spectrum carbon under 80% RH conditions.

The tests are repeated at a relative humidity of 80%. Results are illustrated in FIG. 9 which demonstrate that with BSC alone, breakthrough of NO was immediate. Increasing the MOF depth in the bed increases breakthrough time. At higher humidity, the breakthrough time of NO is faster, however, relative to lower humidity conditions comparing FIG. 9 with FIG. 8. It is also noted that the amount of NO generated under humid conditions is nearly double that observed under dry conditions, but including this the BPL carbon still generates substantially more NO than UiO-66-$NH_2$.

Figure 10:
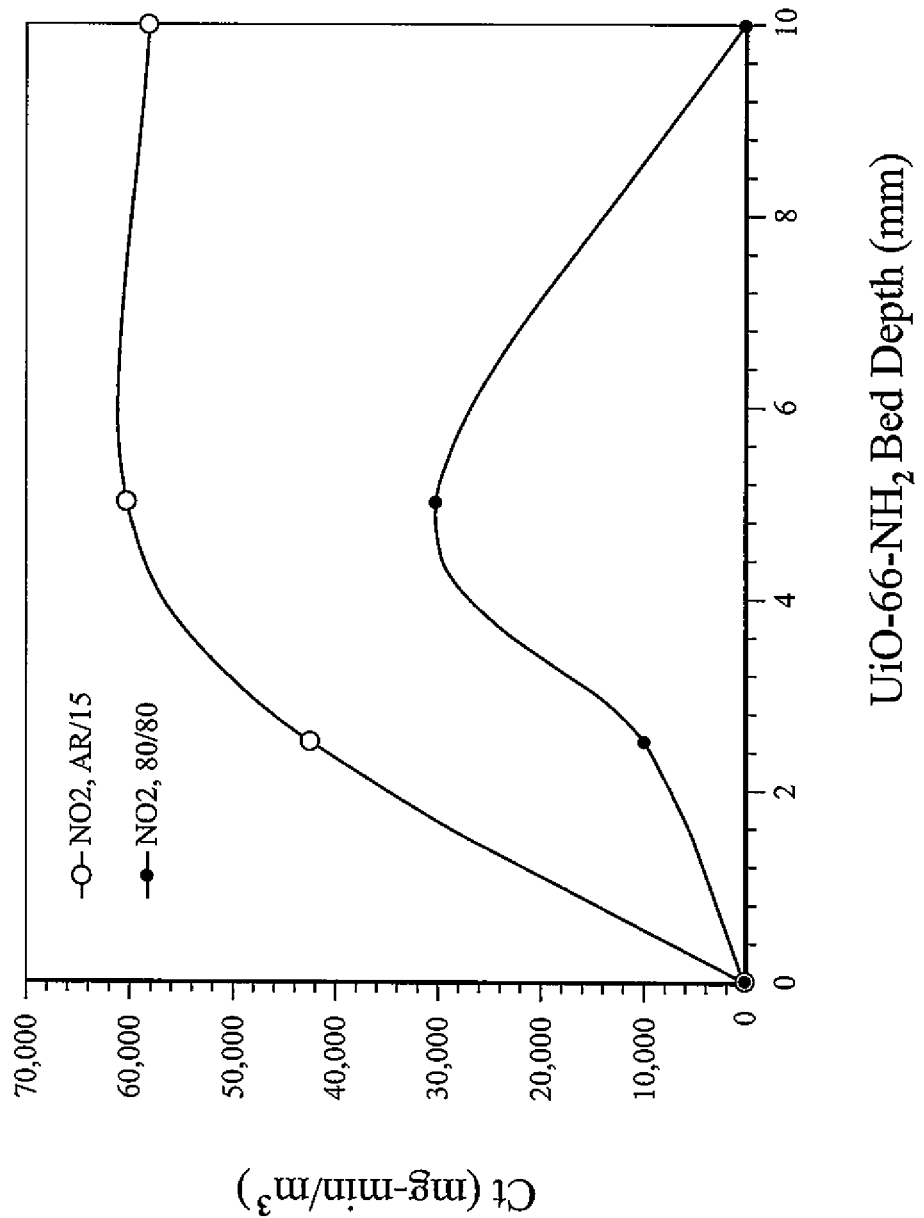
FIG. 10 illustrates various bed depths and the absorption of $NO_2$ ate 15% RH and 80% RH.

Different bed depths of MOF are tested for maximum effectiveness of extending $NO_2$ breakthrough time. As illustrated in FIG. 10, a bed depth of 5 mm produces maximum effectiveness at both 15% RH and 80% RH.

Various modifications of the present invention, in addition to those shown and described herein, will be apparent to those skilled in the art of the above description. Such modifications are also intended to fall within the scope of the appended claims.

It is appreciated that all reagents are obtainable by sources known in the art unless otherwise specified.

Patents, publications, and applications mentioned in the specification are indicative of the levels of those skilled in the art to which the invention pertains. These patents, publications, and applications are incorporated herein by reference to the same extent as if each individual patent, publication, or application was specifically and individually incorporated herein by reference.

The foregoing description is illustrative of particular embodiments of the invention, but is not meant to be a limitation upon the practice thereof. The following claims, including all equivalents thereof, are intended to define the scope of the invention.

I claim:

1. A process for removing nitrogen dioxide from a gaseous sample, comprising:
    moving a gaseous sample including nitrogen dioxide through a filter comprising a filtration media, said filtration media comprising a metal organic framework (MOF), said filtration media suitable to decrease the nitrogen dioxide level in the gaseous sample.

2. The process of claim 1, wherein said MOF includes a functional group capable of reacting with nitrogen dioxide.

3. The process of claim 1, wherein the MOF includes an amine functional group.

4. The process of claim 1, wherein the MOF comprises a UiO-66-$NH_2$.

5. The process of claim 1, wherein said gaseous sample comprises air or combustion exhaust.

6. The process of claim 1, wherein the MOF includes a metal.

7. The process of claim 6, wherein the metal is selected from the group consisting of: Al, Cr, Fe, Hf, Mn, Ti, V, Zr, Ca, and Mg.

8. The process of claim 1, wherein said MOF has an average pore volume of 0.1 cm$^3$/g or greater.

9. The process of claim 1, wherein said MOF has a surface area in excess of 600 m$^2$/g as measured by a Brunauer Emmett Teller (BET) technique.

10. The process of claim 1, wherein said MOF has a capacity for absorbing nitrogen dioxide of 9 moles $NO_2$ per kilogram MOF or greater.

11. The process of claim 1, performed at a reaction temperature of 20 degrees Celsius to 30 degrees Celsius.

12. The process of claim 1, wherein the MOF is combined with a filter material, the filter material comprising carbon.

13. The process of claim 1, wherein the MOF is a component of a building material.

14. A filtration media capable of reducing nitrogen dioxide concentration in a gas sample, comprising:
    a metal organic framework (MOF), wherein said MOF includes a functional group capable of reacting with nitrogen dioxide.

15. The filtration media of claim 14, wherein said functional group comprises an amine functional group.

16. The filtration media of claim 14, wherein said filtration media further includes a carbon filtration media.

17. The filtration media of claim 14, wherein said MOF comprises a UiO-66-$NH_2$.

18. The filtration media of claim 14, wherein said MOF includes a metal.

19. The filtration media of claim 18, wherein the metal is selected from the group consisting of: Al, Cr, Fe, Hf, Mn, Ti, V, Zr, Ca, and Mg.

20. The filtration media of claim 14, wherein said MOF has an average pore volume of 0.1 cm$^3$/g or greater.

21. The filtration media of claim 14, wherein said MOF has a surface area in excess of 600 m$^2$/g as measured by a Brunauer Emmett Teller (BET) technique.

22. The filtration media of claim 14, wherein said MOF has a capacity for absorbing nitrogen dioxide of 9 moles $NO_2$ per kilogram MOF or greater.

23. The filtration media of claim 16, wherein said MOF is located adjacent to the carbon filtration media.

24. The filtration media of claim 16, wherein said MOF is disposed directly on the carbon filtration media proximal to a nitrogen dioxide source.

* * * * *